United States Patent
Elfersy

(10) Patent No.: US 8,999,363 B2
(45) Date of Patent: *Apr. 7, 2015

(54) METHODS AND COMPOSITIONS FOR ANTIMICROBIAL SURFACES

(75) Inventor: Jacques Elfersy, Atlanta, GA (US)

(73) Assignee: Sishield Technologies, Inc., Atlanta, GA (US)

( * ) Notice: Subject to any disclaimer, the term of this patent is extended or adjusted under 35 U.S.C. 154(b) by 1602 days.

This patent is subject to a terminal disclaimer.

(21) Appl. No.: 11/599,956

(22) Filed: Nov. 15, 2006

(65) Prior Publication Data

US 2007/0065475 A1    Mar. 22, 2007

Related U.S. Application Data

(63) Continuation-in-part of application No. 11/349,028, filed on Feb. 7, 2006.

(60) Provisional application No. 60/650,502, filed on Feb. 7, 2005, provisional application No. 60/737,031, filed on Nov. 15, 2005.

(51) Int. Cl.
   *A01N 33/12*   (2006.01)
   *A01N 55/10*   (2006.01)
   *A01N 25/08*   (2006.01)
   *A01N 55/00*   (2006.01)

(52) U.S. Cl.
   CPC .............. *A01N 33/12* (2013.01); *A01N 25/08* (2013.01); *A01N 55/00* (2013.01)

(58) Field of Classification Search
   CPC ....... A01N 33/12; A01N 55/00; A01N 55/08; A01N 2300/00
   USPC ............. 424/405, 616, 421; 514/63, 642, 643
   See application file for complete search history.

(56) References Cited

U.S. PATENT DOCUMENTS

| | | | | |
|---|---|---|---|---|
| 3,247,058 A | * | 4/1966 | Hyman | 424/404 |
| 4,567,039 A | | 1/1986 | Stadnick et al. | |
| 4,908,355 A | | 3/1990 | Gettings et al. | |
| 5,145,596 A | * | 9/1992 | Blank et al. | 510/513 |
| 5,411,585 A | * | 5/1995 | Avery et al. | 106/287.1 |
| 5,833,739 A | * | 11/1998 | Klatte et al. | 95/136 |
| 5,954,869 A | | 9/1999 | Elfersy et al. | |
| 5,959,014 A | | 9/1999 | Liebeskind et al. | |
| 6,113,815 A | | 9/2000 | Elfersy et al. | |
| 6,120,587 A | | 9/2000 | Elfersy et al. | |
| 6,221,944 B1 | | 4/2001 | Liebeskind et al. | |
| 6,469,120 B1 | | 10/2002 | Elfersy et al. | |
| 6,528,472 B2 | * | 3/2003 | Charaf et al. | 510/391 |
| 6,607,717 B1 | | 8/2003 | Johnson et al. | |
| 6,632,805 B1 | | 10/2003 | Liebeskind et al. | |
| 6,712,976 B2 | | 3/2004 | Manzone | |
| 6,762,172 B1 | | 7/2004 | Elfersy et al. | |
| 7,304,022 B2 | * | 12/2007 | Cheung et al. | 510/191 |
| 2003/0100465 A1 | | 5/2003 | Kilkenny et al. | |
| 2004/0099184 A1 | * | 5/2004 | Palm et al. | 106/409 |
| 2004/0182790 A1 | | 9/2004 | Manzone | |
| 2005/0008613 A1 | * | 1/2005 | Peterson et al. | 424/78.27 |
| 2007/0163964 A1 | * | 7/2007 | Williamson et al. | 210/736 |

OTHER PUBLICATIONS

John L. Speier and James R. Malek, "Destruction of Microorganisms by Contact with Solid Surfaces", Journal of Colloid and Interface Science, 1982, 89(1), 68-76.*
A.J. Isquith, E.A. Abbott, and P.A. Walters, "Surface-Bonded Antimicrobial Activity of an Organosilicon Quaternary Ammonium Chloride", Applied Microbiology, 1972, 24(6), 859-863.*
P.A. Walters, E.A. Abbott, and A.J. Isquith, "Algicidal Activity of a Surface-Bonded Organosilicon Quaternary Ammonium Chloride", Applied Microbiology, 1973, 25(2), 253-256.*
The Schundler Company Basic Perlite Information and Data, Schundler Company Perlite Technical Information, www.schundler.com/techperl.htm, pp. 1-3, Aug. 28, 2005.
Schundler Product Guide—Perlite Filter Aids for Liquid/Solid Separation, www.schundler.com/fil-liq.htm, Metuchen, New Jersey, pp. 1-4, Aug. 28, 2005.

* cited by examiner

*Primary Examiner* — John Pak
*Assistant Examiner* — Nathan W Schlientz
(74) *Attorney, Agent, or Firm* — Tim Tingkang Xia, Esq.; Morris, Manning & Martin, LLP

(57) ABSTRACT

The present invention comprises methods and compositions for treating solid surfaces having antimicrobial and biocidal properties. Such surfaces are capable of controlling or killing a broad spectrum of biological agents, including viruses, bacteria and other microbial agents in solids, liquids or gases that subsequently contact the treated surface.

12 Claims, No Drawings

METHODS AND COMPOSITIONS FOR ANTIMICROBIAL SURFACES

RELATED APPLICATIONS

The present application is a continuation-in-part of U.S. patent application Ser. No. 11/349,028, filed Feb. 7, 2006, which claims the priority of U.S. Provisional Patent Application No. 60/650,502, filed Feb. 7, 2005, and the present application claims the priority of U.S. Provisional Patent Application No. 60/737,031, filed Nov. 15, 2005, each of which is herein incorporated in its entirety.

FIELD OF THE INVENTION

The present invention is directed to treated surfaces with antimicrobial properties. In particular, the present invention is directed to making and using treated surfaces with aqueous antimicrobial compositions comprising organosiloxane quaternary ammonium compounds.

BACKGROUND OF THE INVENTION

Humans and animals are exposed to many surfaces that have microbial organisms present, or that may become contaminated with microbial organisms. After the advent of antibiotics, many thought that there were no risks to humans or animals from microbial organisms because antibiotics could solve any infections. Antibiotic resistance soon proved those thoughts to be incorrect. Many microbial organisms are resistant to current therapies and different approaches are needed.

Despite increasing public concern, current technology does not adequately meet the needs. Humans or animals may be exposed to surfaces that are in contact with household contaminating organisms, stormwater, industrial runoff, human and animal waste, and other sources of microbial organisms.

Microbial organisms such as those found in on humans, animals, in sewage, human waste and animal waste, including bacteria, viruses, fungi, and other disease organisms, are of particular concern. Organisms such as pathogenic organisms that are infective at a low organism concentration or whose mode-of-entry may or may not be oral ingestion. These pathogens include, but are not limited to *Pseudomonas aeruginosa, Staphyloccus aureus, Escherichia coli, Shigella*, or enteroviruses. Relatively small populations of *P. aeruginosa* may cause health problems simply through water contact, and such bacteria are typically resistant to antibiotics. The presence of enteroviruses is of concern since very small virus concentrations are capable of producing infections or diseases.

What is needed are methods and compositions for treatment of surfaces with compositions that are capable of controlling or killing a broad spectrum of biological agents, including viruses, bacteria and other microbial agents and then render the surfaces capable of continuing to kill a broad range of microbial agents. The treatments should also be stable, durable with a long lasting effect, safe and non-toxic.

SUMMARY OF THE INVENTION

The present invention provides a composition having antimicrobial activity, where the antimicrobial composition comprises perlite treated or coated with a composition comprising an organosilane quaternary compound (OSQAC) and a quaternary-ammonium compound (QAC), and where the quaternary ammonium compound is not an organosilane quaternary compound. Perlite is admixed with an OSQAC/QAC composition comprising an organosilane quaternary compound and a quaternary ammonium compound, and where the quaternary ammonium compound is not an organosilane quaternary compound, and a portion of the OSQAC/QAC composition coats or adheres to the perlite. The OSQAC/QAC coated perlite may be dried.

In one embodiment, the organosilane quaternary compound is a compound having formula $RnSiX(4-n)$, wherein (1) R is, independently, an alkene group, an alkyl group, or an alkyne group, and (2) X is, independently, an alkoxy group; and where each of the alkene group, the alkyl group, the alkyne group, and the alkoxy group optionally comprises an amino, a chloro, an epoxy, or a mercapto substituent.

In another embodiment, the quaternary ammonium compound comprises at least one compound selected from the group consisting of mono-long-chain, tri-short-chain, tetraalkyl ammonium compounds; di-long-chain, di-short-chain, tetraalkyl ammonium compounds; and trialkyl, mono-benzyl ammonium compounds.

In yet another embodiment, the ratio of organosilane quaternary compound to quaternary ammonium compound may be in a weight range of about 1:100 to about 100:1.

The antimicrobial composition of the present invention may further comprise an OSQAC/QAC composition comprising an oxidizing agent (e.g., hydrogen peroxide, an oxidizing agent such as chlorine or dioxide), a chelating agent (e.g., ethylenediaminetetraacetic acid (EDTA) or a salt thereof), or a stabilizing agent (e.g., sucrose, pentaerythritol, glycol ether, ethanol, or propelyne carbonate). The antimicrobial composition may also comprise an OSQAC/QAC composition comprising other ingredients depending on the application and particular formulation needs and include, but are not limited to, wetting/dispensing agents, propellants, liquefied gases, surfactants, and other formulation components.

Also provided are methods of treating or coating perlite by providing an antimicrobial coating to a surface of the perlite. Methods also comprise making and using the coated or treated perlite and providing long lasting biostatic protection. Methods also comprise providing antimicrobial compositions taught herein for treating or coating a portion of perlite to aid in preventing attachment, colonization or infection and reinfection by microorganisms. The methods of the present invention may also comprise any methods for applying the OSQAC/QAC compositions taught herein to perlite including, without limitation, spraying, dipping, painting, dusting, wiping, dabbing, swabbing, fogging, or misting. In addition, methods also comprise use of the coated or treated perlite.

An OSQAC/QAC composition of the present invention may have the following ingredients:

a. An organosilane quaternary ammonium compound (OSQAC), for example, in a range from about 0.01% to about 42%;

b. A quaternary ammonium compound (QAC) (for example), from about 0.01% to about 32%;

c. Water, as needed, from about 60% to about 99%; optionally;

d. Stabilizer (for example, solvents, polyols, glycol ethers, etc.) and other ingredients as needed for the desired application of the composition, such as, other formulations apparent to those skilled in the art.

Other features and advantages of the present invention will become apparent from the following detailed description. It should be understood, however, that the detailed description and the specific examples, while indicating the preferred embodiments of the invention, are given by way of illustration only, since various changes and modifications within the spirit and scope of the invention will become apparent to those skilled in the art from this detailed description

DETAILED DESCRIPTION

The present invention comprises methods and compositions for treatment of surfaces with compositions that are capable of controlling or killing a broad spectrum of biological agents, including viruses, bacteria, fungi and other microbial agents and rendering the surfaces capable of continuing to kill a broad range of microbial agents. The compositions are stable, durable with a long lasting effect, safe and nontoxic. Compositions of the present invention comprise OSQAC/QAC compositions comprising organosilane quaternary amine compounds and quaternary ammonium compounds, admixed with perlite so that the perlite is coated or treated with the OSQAC/QAC composition. An embodiment of the present invention comprises methods for treating perlite with biocidal or antimicrobial compositions of the present invention to make a biocidal or antimicrobial perlite and methods for using the biocidal or antimicrobial perlite.

The present invention comprises biocidal coating compositions comprising an organosilane quaternary amine compound and at least one additional biocidal active compound. In one embodiment, the organosilane quaternary amine compound includes, but is not limited to, 3-trimethoxysilylpropyltetradecyldimethyl ammonium chloride, 3-trimethoxysilyl propyldidecylmethylammoniumchloride and 3-trihydroxysilyl-propyloctadecyl ammonium. The at least one additional biocidal active compound is one or more compounds includes, but is not limited to, quaternary ammonium compounds, such as chloride and saccharinate quaternary ammonium compounds from Lonza or Stepan Co., antibiotics, antivirals, antifungals, and antimicrobials.

An OSQAC/QAC composition of the present invention may comprise an organosilane quaternary compound and a quaternary ammonium compound and may include, but is not limited to, mono-long-chain, tri-short-chain, tetraalkyl ammonium compounds, di-long-chain, di-short-chain tetraalkyl ammonium compounds, trialkyl, mono-benzyl ammonium compounds and any mixtures thereof. The quaternary ammonium compound may include but is not limited to, the Bardac series compounds such as Bardac MB 2050, Lonza compounds and product series such as 208, and Stepan Co. product series and compounds such as 2125. The quaternary ammonium compound may comprise either chloride or saccharinate counterions, or, a mixture thereof. An OSQAC/QAC composition may comprise one or more different organosilane quaternary compounds together with one or more different quaternary ammonium compounds.

OSQAC/QAC compositions of the present invention may further comprise stabilizer compounds. Several compounds and methods of stabilizing organosilane quaternary compounds are known in the art, and include methods described in U.S. Pat. Nos. 5,954,869; 5,959,014; 6,120,587; 6,113,815; 6,469,120; and 6,762,172. Additional methods are described in U.S. patent application Ser. No. 10/392,746. In one embodiment, the organosilane quaternary compound may be stabilized by the reaction in propylene carbonate. An advantage of stabilized organosilane quaternary compounds is the ability to deliver silanes in an aqueous solution to commonly encountered surfaces. Compositions used in methods of the present invention may also comprise an organosilane quaternary ammonium compound and an organosilane provided in emulsions such as those taught in U.S. Pat. Nos. 4,908,355 and 6,607,717.

Compositions of the present invention may comprise an organosilane quaternary compound and a quaternary ammonium compound, which when combined can provide contact disinfection and residual antimicrobial activity when coated on perlite; and may further comprise an oxidizing agent and a chelating agent, and water or other solvent. Examples include, but are not limited to, compositions wherein the oxidizing agent is hydrogen peroxide and the chelating agent is EDTA.

The present invention comprises OSQAC/QAC compositions comprising an organosilane quaternary compound and a quaternary ammonium compound, and may further comprise an oxidizing agent or a chelating agent, and may optionally comprise a surfactant; a wetting agent; an antibiotic compound, antifungal agent, or an antiviral agent. OSQAC/QAC compositions of the present invention also comprise an organosilane quaternary compound and may further comprise one or more of, a surfactant; a wetting agent; an antibiotic compound, antifungal agent, an antiviral agent, an oxidizing agent or a chelating agent.

OSQAC/QAC compositions of the present invention comprise a ratio of organosilane quaternary compound to one or more quaternary ammonium compounds in a weight range of 1:100 to 100:1 or in a weight range of 1:10 to 10:1. The ratio of organosilane quaternary compound to one or more quaternary ammonium compounds may be determined by the particular use of the composition or final product or the surface or material to which the composition is to be applied, as well as the specific nature of the microbial contamination or potential microbial contamination.

OSQAC/QAC compositions may comprise water, an aqueous or non aqueous solvent, or combinations or aqueous and nonaqueous solvents in a range between about 50% to about 80%, by weight; organosilane quaternary compound in a concentration range of about 0.001% to about 85%; one or more quaternary ammonium compounds in a concentration range of about 0.001% to about 10%; and optionally, chelating agent such as EDTA in a concentration range of about 0% to about 5%; reducing agent such as hydrogen peroxide in a concentration range of about 0% to about 5%; solubility enhancing agents or other formulation agents such as isopropyl alcohol in a concentration range of about 0% to about 10%, solvent enhancers such as glycol ether in a concentration range of about 0% to about 10%; and wetting agents such as NP-9 (Nanophenol Ethoxylate-9) in a concentration range of about 0% to about 10%.

An OSQAC/QAC composition may comprise about 60-90% water; an organosilane quaternary compound in a concentration range of about 0.001% to about 6%; one or more quaternary ammonium compounds in a concentration range of about 0.001% to about 5%; EDTA at a concentration of range of about 0.1% to about 3%; hydrogen peroxide at a concentration range of about 0.01% to about 3%; isopropyl alcohol at a concentration range of about 5% to about 7%; Glycol Ether DB at a concentration range of about 0.1% to about 7%; and NP-9 at a concentration range of about 0.1% to about 4%.

The organosilane quaternary compound may be any suitable organosilanes known to one skilled in the art, including, without limitation, the organosilanes taught by U.S. Pat. Nos. 5,954,869; 5,959,014; 6,120,587; 6,113,815; 6,469,120; 6,221,944; 6,607,717 and 6,762,172, and U.S. patent application Ser. No. 10/392,746. In one embodiment, the organosilane quaternary compound may include, without limitation, an organosilane compound of formula $R_nSiX_{(4-n)}$, where, n is an integer of from 0 to 3;

R is, independently, an alkene group, an alkyl group, or an alkyne group; and

X is, independently, an alkoxy group.

Each of the alkene group, the alkyl group, the alkyne group, and the alkoxy group may optionally comprise an amino, a chloro, an epoxy, or a mercapto substituent. Other organosilane quaternary amines for use in the compounds, products and compositions and methods of the present invention comprise organosilane quaternary amine compounds of the following formula:

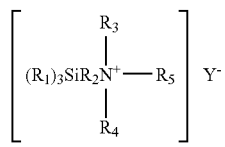

wherein each $R_1$ is, independently, halogen [Cl, Br, I, F] or $R_6O$, where $R_6$ is H, alkyl of from 1 to about 6 carbon atoms, unsubstituted or substituted, preferably from 1 to about 2 carbon atoms and more preferably 1 carbon atom, or acetyl- or other acyl, including substituted acyl and acyloxy; or $R_6O$ can be derived from any hydroxylated polymer, hydroxylated liquid, or hydroxylated solid regardless of water solubility; or $R_6O$ can be derived from any polyglycol such as, but not limited to, polyethyleneglycols or polypropyleneglycols, such as poly(propyleneglycol)triol (glycerol propoxylate); $R_2$ is unsubstituted or substituted benzyl- or an unsubstituted or substituted alkyl of from 1 to about 3 carbon atoms, preferably alkyl of from 1 to 3 carbon atoms; $R_3$ and $R_4$ are, independently, lower alkoxy of from 1 to 4 carbon atoms, preferably of 2 carbon atoms, such as $CH_2CH_2OH$, $CH_2CH(OH)CH_3$, alkyl of from 1 to about 22 carbon atoms, preferably from 1 to about 10 carbon atoms and most preferably from 1 to 2 carbon atoms or $R_3$ and $R_4$ can, together, form a morpholine or other cyclic or heterocyclic, unsaturated or saturated, five to seven-membered ring of the formula:

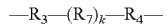

where k is an integer from 0 to 2 and $R_7$, where the ring is saturated, is $CH_2$, O, S, NH, $NH_2^+$, $NCH_2CH_2NH_2$, $NCH_2CH_2NH_3^+$, $NCH_2CH_2N(R_8)(R_9)$, $NCH_2CH_2N^+(R_8)(R_9)(R_{10})$, N(alkyl), N(aryl), N(benzyl), and $R_7$, where the ring is unsaturated is, N, $N^+H$, $N^+$(alkyl), $N^+$(aryl), $N^+$(benzyl), N—$CH_2$—N, $N^+H$—$CH_2$—N, $N^+$(alkyl)-$CH_2$—N, $N^+$(aryl)-$CH_2$—N, or $N^+$(benzyl)-$CH_2$—N where $R_8$, $R_9$, and R (10) are, independently, benzyl, polyglycol, lower alkyl alcohol of from 1 to 4 carbon atoms, lower alkoxy of from 1 to 4 carbon atoms, or alkyl of from 1 to about 22 carbon atoms, preferably 1 to about 10 carbon atoms; $R_5$ is $CH_2C_6H_5$, $CH_2CH_2OH$, $CH_2CH(OH)CH_3$, a polyglycol such as polyethyleneglycol: —$(CHCH_2O)H$, polypropyleneglycol: —$(CH_2CH(CH_3)O)_aH$, or alkylated polyoxyethylene: —$(CH_2CH_2O)_aB$ where B is alkyl of from 1 to 22 carbon atoms, unsubstituted or substituted, and where each a is, independently, an integer of from 1 to 12, more preferably of from about 1 to about 5, or $R_5$ is alkyl or perfluoroalkyl of from 1 to about 22 carbon atoms, preferably from 12 to about 20 carbon atoms and even more preferably from 14 to about 18 carbon atoms; and Y is halogen (such as Cl, Br, I), acetate, sulfate, tosylate or carboxylate, such as acetate, polycarboxylate salts, alcoholates, functionalized carboxylate, such as trifluoroacetate and perfluoroalkylcarboxylates, or other alkyl and arylsulfonate salts, including trifluoromethylsulfonate and anionic metal oxides, perfluoroalkylsulfonate salts, phosphate and phosphonate salts, borate and boronate salts, benzoates or any other suitable anionic moiety and the ring provided for formula V represents $R_3$ or $R_4$, independently, with the ring nitrogen of formula II or III replaced by CH or $CH_2$. This ring is attached to the nitrogen in structure II or III, by removing any one hydrogen from the structure and placing a bond from the nitrogen of II or III to the atom missing the hydrogen.

Organosilane quaternary amines of the present invention may comprise one or more of the following:

3-(trimethoxysilyl)propyldimethyloctadecyl ammonium chloride, 3-(trimethoxysilyl)propylmethyldi(decyl)ammonium chloride, 3-(trihydroxysilyl)propyl-dimethyloctadecyl ammonium chloride octadecyltrimethoxysilane, perfluorooctyltriethoxysilane, aminoethylaminopropyltrimethoxysilane, 3-aminopropyltrimethoxysilane, 3-aminopropyltriethoxysilane, 3-chloropropyltrimethoxysilane, 3-chloropropyltriethoxysilane, 3-chloropropyltrichlorosilane, 3-glycidoxypropyltrimethoxysilane, 3-glycidoxypropyltriethoxysilane, 3-methacryloxypropyltriethoxysilane, 3-methacryloxypropyltrimethoxysilane, methyldichlorosilane, sodium (trihydroxysilyl)propylmethylphosphonate, trichlorosilane, n-2-vinylbenzylamino-ethyl-3-aminopropyltrimethoxysilane HCL, vinyltriacetoxysilane, vinyltrimethoxysilane, vinyltriethoxysilane, vinyltrichlorosilane, dimethyldichlorosilane, dimethyldimethoxysilane, diphenyldichlorosilane, ethyltrichlorosilane, ethyltrimethoxysilane, ethyltriethoxysilane, isobutyltrimethoxysilane, n-octyltriethoxysilane, methylphenyldichlorosilane, methyltrichlorosilane, methyltrimethoxysilane, phenyltrichlorosilane, phenyltrimethoxysilane, n-propyltrichlorosilane, n-propyltrimethoxysilane, silicon tetrachloride, decyltrichlorosilane, dichloromethyl(4-methylphenethyl)silane, diethoxymethylphenylsilane,

[3-(diethylamino)propyl]trimethoxysilane, 3-(dimethoxymethylsilyl)-1-propanethiol, dimethoxymethylvinylsilane, 3-[tris(trimethylsilyloxy)silyl]propyl methacrylate, trichloro[4-(chloromethyl)phenyl]silane, methylbis(trimethylsilyloxy)vinylsilane, methyltripropoxysilane, trichlorocyclopentylsilane, $(CH_3O)_3Si(CH_2)_3N^+(CH_3)_2C_{18}H_{37}Cl^-$,
$(CH_3O)_3Si(CH_2)_3N^+(CH_3)_2C_{18}H_{37}Br^-$,
$(CH_3O)_3Si(CH_2)_3N^+(C_{10}H_{21})CH_3Cl^-$,
$(CH_3O)_3Si(CH_2)_3N^+(C_{10}H_{21})CH_3Br^-$,
$(CH_3O)_3Si(CH_2)_3N^+(CH_3)_3Cl^-$,
$(CH_3O)_3Si(CH_2)_3N^+(CH_3)_2C_8H_{17}Cl^-$,
$(CH_3O)_3Si(CH_2)_3N^+(CH_3)_2C_{10}H_{21}Cl^-$,
$(CH_3O)_3Si(CH_2)_3N^+(CH_3)_2C_{12}H_{25}Cl^-$,
$(CH_3O)_3Si(CH_2)_3N^+(CH_3)_2C_{14}H_{29}Cl^-$,
$(CH_3O)_3Si(CH_2)_3N^+(CH_3)_2C_{16}H_{33}Cl^-$,
$(CH_3O)_3Si(CH_2)_3N^+(CH_3)_2C_{20}H_{41}Cl^-$,
$(CH_3O)_3Si(CH_2)_3N^+(CH_4H_9)_3Cl^-$,
$(CH_3O)_3Si(CH_2)_3N^+(C_2H_5)_3Cl^-$,
$(CH_3CH_2O)_3Si(CH_2)_3N^+(CH_3)_2C_{18}H_{27}Cl^-$,
$(CH_3O)_3Si(CH_2)_3N^+(CH_3)_2(CH_2)_3NHC(O)(CH_2)_6CH_3Cl^-$,
$(CH_3O)_3Si(CH_2)_3N^+(CH_3)_2(CH_2)_3NHC(O)(CH_2)_8CH_3Cl^-$,
$(CH_3O)_3Si(CH_2)_3N^+(CH_3)_2(CH_2)_3NHC(O)(CH_2)_{10}CH_3Cl^-$,
$(CH_3O)_3Si(CH_2)_3N^+(CH_3)_2(CH_2)_3NHC(O)(CH_2)_{12}CH_3Cl^-$,
$(CH_3O)_3Si(CH_2)_3N^+(CH_3)_2(CH_2)_3NHC(O)(CH_2)_{14}CH_3Cl^-$,
$(CH_3O)_3Si(CH_2)_3N^+(CH_3)_2(CH_2)_3NHC(O)(CH_2)_{16}CH_3Cl^-$,
$(CH_3O)_3Si(CH_2)_3N^+(CH_3)_2(CH_2)_3NHC(O)(CF_2)_6CF_3, Cl^-$
$(CH_3O)_3Si(CH_2)_3N^+(CH_3)_2(CH_2)_3NHC(O)(CF_2)_8CF_3Cl^-$,
$(CH_3O)_3Si(CH_2)_3N^+(CH_3)_2(CH_2)_3NHC(O)(CF_2)_{10}CF_3Cl^-$,
$(CH_3O)_3Si(CH_2)_3N^+(CH_3)_2(CH_2)_3NHC(O)(CF_2)_{12}CF_3Cl^-$,
$(CH_3O)_3Si(CH_2)_3N^+(CH_3)_2(CH_2)_3NHC(O)(CF_2)_{14}CF_3Cl^-$,
$(CH_3O)_3Si(CH_2)_3N^+(CH_3)_2(CH_2)_3NHC(O)(CF_2)_{16}CF_3Cl^-$,
$(CH_3O)_3Si(CH_2)_3N^+(CH_3)_2(CH_2)_3NHC(O)(CF_2)_7CF_3Cl^-$,
$(CH_3O)_3Si(CH_2)_3N^+(CH_3)_2(CH_2)_3NHSO_2(CF_2)_9CF_3Cl^-$,
$(CH_3O)_3Si(CH_2)_3N^+(CH_3)_2(CH_2)_3NHSO_2(CF_2)_7CF_3Cl^-$,
$(CH_3O)_3Si(CH_2)_3N^+(CH_3)_2(CH_2)_3NHSO_2(CF_2)_{11}CF_3Cl^-$,
$(CH_3O)_3Si(CH_2)_3N^+(CH_3)_2(CH_2)_3NHSO_2(CF_2)_{13}CF_3Cl^-$,
$(CH_3O)_3Si(CH_2)_3N^+(CH_3)_2(CH_2)_3NHSO_2(CF_2)_{15}CF_3Cr^-$,
$(CH_3O)_3Si(CH_2)_3N^+(CH_3)_2(CH_2)_3NHSO_2(CF_2)_{16}CF_3Cl^-$, Also contemplated by the present invention are organosilane quaternary amines comprising functional groups such as para-amino benzoic acid, cinnamic acid, benzoic acid and benzophenone, including, but not limited to the following:

$(CH_3O)_3Si(CH_2)_3NHC_6H_4COOCH_2C_6H_4N^+(CH_3)_3Cl^-$
$(CH_3O)_3Si(CH_2)_3NHC_6H_4COOCH_2C_6H_4N^+(CH_2CH_3)_3Cl^-$
$(CH_3O)_3Si(CH_2)_3NCH_3C_6H_4COOCH_2C_6H_4N^+(CH_3)_3Cl^-$
$(CH_3O)_3Si(CH_2)_3NCH_3C_6H_4COOCH_2C_6H_4N^+(CH_2CH_3)_3Cl^-$
$(CH_3O)_3Si(CH_2)_3N^+(CH_3)_2C_6H_4COOHCl^-$
$(CH_3O)_3Si(CH_2)_3N^+(CH_3)_2C_6H_4COOCH_3Cl^-$
$(CH_3O)_3Si(CH_2)_3N^+(CH_3)_2C_6H_4COOC_2H_5Cl^-$
$(CH_3O)_3SI(CH_2)_3N^+(CH_3)_2C_6H_4COOC_3H_7Cl^-$
$(CH_3O)_3Si(CH_2)_3N^+(CH_3)_2C_6H_4COOC_4H_9Cl^-$
$(CH_3O)_3Si(CH_2)_3N^+(CH_3)_2C_6H_4COOCH_2C_6H_5Cl^-$
$(CH_3O)_3Si(CH_2)_3N^+(CH_3)_2C_6H_4COOCH_2C_6H_4N_2Cl^-$
$(CH_3O)_3Si(CH_2)_3N^+(CH_3)_2C_6H_4COOCH_2C_6H_4N(CH_3)_2 Y^-$
$(CH_3O)_3Si(CH_2)_3N^+(CH_3)_2C_6H_4COOCH_2C_6H_4N(CH_2CH_3)_2Cl^-$
$(CH_3O)_3Si(CH_2)_3N^+(CH_3)_2C_6H_4COOCH_2C_6H_4N^+(CH_3)_3Cl^-Cl^-$
$(CH_3O)_3Si(CH_2)_3N^+(CH_3)_2C_6H_4COOCH_2C_6H_4N^+(CH_2CH_3)_3Cl^-Cl^-$
$(CH_3O)_3Si(CH_2)_3N^+(C_2H_5)_2C_6H_4COOHCl^-$
$(CH_3O)_3Si(CH_2)_3N^+(C_2H_5)_2C_6H_4COOCH_3Cl^-$
$(CH_3O)_3Si(CH_2)_3N^+(C_2H_5)_2C_6H_4COOC_2H_5Cl^-$
$(CH_3O)_3Si(CH_2)_3N^+(C_2H_5)_2C_6H_4COOC_3H_7Cl^-$
$(CH_3O)_3Si(CH_2)_3N^+(C_2H_5)_2C_6H_4COOC_4H_9Cl^-$
$(CH_3O)_3Si(CH_2)_3N^+(C_2H_5)_2C_6H_4COOCH_2C_6H_5Cl^-$
$(CH_3O)_3Si(CH_2)_3N^+(C_2H_5)_2C_6H_4COOCH_2C_6H_4N_2Cl^-$
$(CH_3O)_3Si(CH_2)_3N^+(C_2H_5)_2C_6H_4COOCH_2C_6H_4N(CH_3)_2 Cl^-$
$(CH_{30})_3Si(CH_2)_3N^+(C_2H_5)_2C_6H_4COOCH_2C_6H_4N(CH_2CH_3)_2Cl^-$
$(CH_3O)_3Si(CH_2)_3N^+(C_2H_5)_2C_6H_4COOCH_2C_6H_4N^+(CH_3)_3Cl^{-Cl-}$
$(CH_3O)_3Si(CH_2)_3N^+(C_2H_5)_2C_6H_4COOCH_2C_6H_4N^+(CH_2CH_3)_3Cl^-Cl^-$
$(CH_3CH_2O)_3Si(CH_2)_3NCH_3C_6H_4COOCH_2C_6H_4N^+(CH_3)_3Cl^-$
$(CH_3CH_2O)_3Si(CH_2)_3NCH_3C_6H_4COOCH_2C_6H_4N^+(CH_2CH_3)_3Cl^-$
$(CH_3CH_2O)_3Si(CH_2)_3N^+(CH_3)_2C_6H_4COOHCl^-$
$(CH_3CH_2O)_3Si(CH_2)_3N^+(CH_3)_2C_6H_4COOCH_3Cl^-$
$(CH_3CH_2O)_3Si(CH_2)_3N^+(CH_3)_2C_6H_4COOC_2H_5Cl^-$
$(CH_3CH_2O)_3Si(CH_2)_3N^+(CH_3)_2C_6H_4COOC_3H_7Cl^-$
$(CH_3CH_2O)_3Si(CH_2)_3N^+(CH_3)_2C_6H_4COOC_4H_9Cl^-$
$(CH_3CH_2O)_3Si(CH_2)_3N^+(CH_3)_2C_6H_4COOCH_2C_6H_5Cl^-$
$(CH_3CH_2O)_3Si(CH_2)_3N^+(CH_3)_2 C_6H_4COOCH_2C_6H_4NH_2Cl^-$
$(CH_3CH_2O)_3Si(CH_2)_3N^+(CH_3)_2C_6H_4COOCH_2C_6H_4N(CH_3)_2Cl^-$
$(CH_3CH_2O)_3Si(CH_2)_3N^+(CH_3)_2C_6H_4COOCH_2C_6H_4N(CH_2CH_3)_2Cl^-$
$(CH_3CH_2O)_3Si(CH_2)_3N^+(CH_3)_2C_6H_4COOCH_2C_6H_4N^+(CH_3)_3Cl^{-Cl-}$
$(CH_3CH_2O)_3Si(CH_2)_3N^+(CH_3)_2C_6H_4COOCH_2C_6H_4N^+(CH_2CH_3Cl^{-Cl-}$
$(CH_3O)_3Si(CH_2)_3NHC(O)(CF_2)_6CF_3$,
$(CH_3O)_3Si(CH_2)_3NHC(O)(CF_2)_8CF_3$
$(CH_3O)_3Si(CH_2)_3NHC(O)(CF_2)_{10}CF_3$
$(CH_3O)_3Si(CH_2)_3NHC(O)(CF_2)_{12}CF_3$
$(CH_3O)_3Si(CH_2)_3NHC(O)(CF_2)_{14}CF_3$
$(CH_3O)_3Si(CH_2)_3NHC(O)(CF_2)_{16}CF_3$
$(CH_3O)_3Si(CH_2)_3NHC(O)(CF_2)_6CF_3$
$(CH_3O)_3Si(CH_2)_3NHSO_2(CF_2)_7CF_3$,
$(CH_3O)_3Si(CH_2)_3N^+(CH_3)_2(CH_2)_3NHC(O)(CF_2)_6CF_3$,
$(CH_3O)_3Si(CH_2)_3N^+(CH_3)_2(CH_2)_3NHC(O)(CF_2)_8CF_3$,
$(CH_3O)_3Si(CH_2)_3N^+(CH_3)_2(CH_2)_3NHC(O)(CF_2)_{10}CF_3^-$,
$(CH_3O)_3Si(CH_2)_3N^+(CH_3)_2(CH_2)_3NHC(O)(CF_2)_{12}CF_3$,
$(CH_3O)_3Si(CH_2)_3N^+(CH_3)_2(CH_2)_3NHC(O)(CF_2)_{14}CF_3$,
$(CH_3O)_3Si(CH_2)_3N^+(CH_3)_2(CH_2)_3NHC(O)(CF_2)_{16}CF_3$,
$(CH_3O)_3Si(CH_2)_3N^+(CH_3)_2(CH_2)_3NHC(O)(CF_2)_7CF_3$,
$(CH_3O)_3Si(CH_2)_3N^+(CH_3)_2(CH_2)_3NHSO_2(CF_2)_9CF_3$,
$(CH_3O)_3Si(CH_2)_3N^+(CH_3)_2(CH_2)_3NHSO_2(CF_2)_{11}CF_3$,
$(CH_3O)_3Si(CH_2)_3N^+(CH_3)_2(CH_2)_3NHSO_2(CF_2)_{13}CF_3$,
$(CH_3O)_3Si(CH_2)_3N^+(CH_3)_2(CH_2)_3NHSO_2(CF_2)_{15}CF_3$,
$(CH_3O)_3Si(CH_2)_3N^+(CH_3)_2(CH_2)_3NHSO_2(CF_2)_{16}CF_3$
$(CH_3CH_2O)_3Si(CH_2)_3N^+(C_2H_5)_2C_6H_4COOHCl^-$ $(CH_3CH_2O)_3Si(CH_2)_3N^+(C_2H_5)_2C_6H_4COOCH_3Cl^-$
$(CH_3CH_2O)_3Si(CH_2)_3N^+(C_2H_5)_2C_6H_4COOC_2H_5Cl^-$
$(CH_3CH_2O)_3Si(CH_2)_3N^+(C_2H_5)_2C_6H_4COOC_3H_7Cl^-$
$(CH_3CH_2O)_3Si(CH_2)_3N^+(C_2H_5)_2C_6H_4COOCH_2C_4H_9Cl^-$
$(CH_3CH_2O)_3Si(CH_2)_3N^+(C_2H_5)_2C_6H_4COOCH_2C_6H_5Cl^-$
$(CH_3CH_2O)_3Si(CH_2)_3N^+(C_2H_5)_2C_6H_4COOCH_2C_6H_4NH_2Cl^-$
$(CH_3CH_2O)_3Si(CH_2)_3N^+(C_2H_5)_2C_6H_4COOCH_2C_6H_4N(CH_3)_2Cl^-$
$(CH_3CH_2O)_3Si(CH_2)_3N^+(C_2H_5)_2C_6H_4COOCH_2C_6H_4N(CH_2CH_3)_2Cl^-$
$(CH_3CH_2O)_3Si(CH_2)_3N^+(C_2H_5)_2C_6H_4COOCH_2C_6H_4N^+(CH_3)_3Cl^{-Cl-}$, and
$(CH_3CH_2O)_3Si(CH_2)_3N^+(C_2H_5)_2C_6H_4COOCH_2C_6H_4N^+(CH_2CH_3)_3Cl^{-Cl-}$.

$NH_2(CH_2)_2NH(CH_2)_3Si(OCH_3)_3$,
$NH_2(CH_2)_3Si(OCH_3)_3$,
$NH_2(CH_2)_3Si(OCH_2CH_3)_3$,
$Cl(CH_2)_3Si(OCH_3)_3$,
$Cl(CH_2)_3Si(OCH_2CH_3)_3$,
$Cl(CH_2)_3SiCl_3$,
$CH_3CH_2C(O)O-(CH_2)_3Si(OCH_3)_3$,
$CH_3CH_2C(O)O-(CH_2)_3Si(OCH_2CH_3)_3$,
$CH_3SiHCl_2$,
$NaO(CH_3O)P(O)(CH_2)_3Si(OH)_3$,
$SiHCl_3$,
$(CH_3)_2Si(OCH_3)_2$,
$(C_6H_5)_2SiCl_2$,
$(C_2H_5)SiCl_3$,
$(C_2H_5)Si(OCH_3)_3$,
$(C_2H_5)Si(OCH_2CH_3)_3$,
$CH_3(C_6H_5)SiCl_2$,
$CH_3SiCl_3$,
$CH_3Si(OCH_3)_3$,
$C_6H_5SiCl_3$,
$C_6H_5Si(OCH_3)_3$,
$C_3H_7SiCl_3$,
$C_3H_7Si(OCH_3)_3$,
$SiCl_4$,
$ClCH_2C_6H_4CH_2CH_2SiCl_3$,
$ClCH_2C_6H_4CH_2CH_2Si(OCH_3)_3$,
$ClCH_2C_6H_4CH_2CH_2Si(OCH_2CH_3)_3$,
(decyl)(trichloro)silane,
(dichloro)(methyl)(4-methylphenethyl)silane,
(diethoxy)(methyl)(phenyl)silane,
{3-(diethylamino)propyl}(trimethoxy)silane,
{3-(dimethoxy)(methyl)silyl}-1-propanethiol,
(dimethoxy)(methyl)(vinyl)silane, 3-{tris(trimethylsilyloxy)silyl}propyl
  methacrylate, (trichloro){4-(chloromethyl)phenyl}silane,
  (methyl){bis(trimethylsilyloxy)}(vinyl)silane, (methyl)(tripropoxy)silane,
  (trichloro)(cyclopentyl)silane
  isobutyltrimethoxysilane,
  n-octyltriethoxysilane,
$H_2C=C(CH_3)C(O)O-(CH_2)_3Si(OCH_3)_3$,
$H_2C=C(CH_3)C(O)O-(CH_2)_3Si(OCH_2CH_3)_3$,
$H_2C=CHSi(OCOCH_3)_3$,
$H_2C=CHSi(OCH_3)_3$,
$H_2C=CHSi(OCH_2CH_3)_3$,
$H_2C=CHSiCl_3,(CH_3)_2SiCl_2$, The compositions of the present invention comprise organosilane compositions taught by U.S. Pat. No. 6,632,805 which is herein incorporated in its entirety.

In an embodiment, the organosilane quaternary ammonium compound (OSQAC) may be 3-trimethoxysilyl propyltetradecyldimethyl ammonium chloride, 3-trimethoxysilyl propyldidecylmethyl ammonium chloride, or 3-trihydroxysilyl propyloctadecyl ammonium chloride. In an embodiment, the antimicrobial composition of the present invention may contain organosilane quaternary compounds in a concentration range of about 0.01-10% by weight, more preferably about 0.01-2%. Two commercially relevant examples of organosilane quaternary compounds are SiS AM7200 (72% active) and Dow Corning 5700 (42% active) manufactured by SiShield Technologies, Inc., Atlanta, Ga. and Dow Corning Corporation, Midland, Mich., respectively.

The OSQAC/QAC compositions of the present invention may comprise OSQAC in a range of from about 0.01% to about 42%, from about 0.01% to about 32%; from about 0.01% to about 25.0%; from about 0.01% to about 22%; from about 0.01% to about 12%; from about 0.01% to about 10%; from about 0.01% to about 6.0%; from about 0.01% to about 5.0%; from about 0.01% to about 4.0%; from about 0.01% to about 3.0%; from about 0.01% to about 2.0%; from about 0.01% to about 1.0%; from about 0.01% to about 0.1%; from about 1.0% to about 42%; from about 10% to about 42%; from about 20% to about 42%; and from about 30% to about 42%. The OSQAC may be about 72% active as made, such as the Sishield product above, as this activity is commonly understood by those skilled in the art, or the OSQAC may be about 42%, such as the DOW product above, or the OSQAC may have any active amount that is capable of being formed during synthesis. The compositions of the present invention may comprise QAC, which may comprise an individual type or one QAC or a mixture or combination of different QACs in a range of from about 0.01% to about 32%; from about 0.01% to about 28%; from about 0.01% to about 25.0%; from about 0.01% to about 22%; from about 0.01% to about 12%; from about 0.01% to about 10%; from about 0.01% to about 6.0%; from about 0.01% to about 5.0%; from about 0.01% to about 4.0%; from about 0.01% to about 3.0%; from about 0.01% to about 2.0%; from about 0.01% to about 1.0%; from about 0.01% to about 0.1%; from about 1.0% to about 32%; from about 10% to about 32%; from about 20% to about 32%; and from about 28% to about 32%.

The one or more quaternary ammonium compounds (QAC) may be any quaternary ammonium compound suitable for the purposes of the present invention known to a person skilled in the art, including, without limitation, mono-long-chain, tri-short-chain, tetraalkyl ammonium compounds; di-long-chain, di-short-chain, tetraalkyl ammonium compounds; and trialkyl, mono-benzyl ammonium compounds. Examples of such quaternary ammonium compounds include, without limitation, the Bardac series compounds such as BARDAC® MB 2050 (N,N-Dialkyl($C_{8-10}$)-N-N-dimethyl ammonium, 40% ethanol/10% water), made by Lonza, Lonza compounds and product series such as 208M (32% Alkyl ($C_{14}$ 50%, $C_{12}$ 40%, $C_{16}$ 10%) Dimethyl benzyl ammonium chloride, 24% octyl decyl dimethyl ammonium chloride, 9.6% Dioctyl dimethyl ammonium chloride, 14.4% Didecyl dimethyl ammonium chloride, 10% ethyl alcohol, and 10% water), and Stepan Co. product series and compounds such as BTC 2125. For example, QAC may comprise BTC® 1010 Didecyl dimethyl ammonium chloride; BTC® 1010-80% Didecyl dimethyl ammonium chloride; BTC® 1218-50 Alkyl dimethyl benzyl ammonium chloride (<10% $C_8$+$C_{10}$, 50% $C_{12}$, 19% $C_{14}$, 9% $C_{16}$, 8% $C_{18}$); BTC® 1218-80E Alkyl dimethyl benzyl ammonium chloride (<10% $C_8$+$C_{10}$, 50% $C_{12}$, 19% $C_{14}$, 9% $C_{16}$, 8% $C_{18}$); BTC® 2050 Didecyldimethyl ammonium chloride; BTC® 2125M n-Alkyl dimethyl benzyl ammonium chlorides (and) n-Alkyl dimethyl ethylbenzyl ammonium chlorides; BTC® 2125M P40 n-Alkyl dimethyl benzyl ammonium chlorides and n-Alkyl dimethyl ethylbenzyl ammonium chlorides; BTC® 2125M 80% n-Alkyl dimethyl benzyl ammonium chlorides and n-Alkyl dimethyl ethylbenzyl ammonium chlorides; BTC® 2125M 90% n-Alkyl dimethyl benzyl ammonium chlorides and n-Alkyl dimethyl ethylbenzyl ammonium chlorides; BTC® 50 n-Alkyl dimethyl benzyl ammonium chloride; BTC® 65 n-Alkyl dimethyl benzyl ammonium chloride; BTC® 818 Dialkyl dimethyl ammonium chloride; BTC® 818 80% Dialkyl dimethyl ammonium chloride; BTC® 824 n-Alkyl dimethyl benzyl ammonium chloride; BTC® 8248 n-Alkyl dimethyl benzyl ammonium chloride; BTC® 8249 n-Alkyl dimethyl benzyl ammonium chloride; BTC® 835 n-Alkyl dimethyl benzyl ammonium chloride; BTC® 8358 n-Alkyl dimethyl benzyl ammonium chloride; BTC® 885 n-Alkyl dimethyl benzyl ammonium chloride and Dialkyldimethyl ammonium chloride; BTC® 888 n-Alkyl dimethyl benzyl ammonium chloride and Dialkyl dimethyl ammonium chloride; BTC® D 80 Alkyl dimethyl benzyl ammonium chloride (<10% $C_8+C_{10}$, 50% $C_{12}$, 19% $C_{14}$, 9% $C_{16}$, 8% $C_{18}$).

In one embodiment, the quaternary ammonium compound may further comprise a chloride or a saccharinate counterion, or a combination thereof. In another embodiment, the composition of the present invention may contain quaternary ammonium compounds in a concentration range of about 0.01-5%, or about 0.1-2%. In still another embodiment, the composition of the present invention may comprise a ratio of organosilane quaternary compound to quaternary ammonium compound in a weight range of about 1:100 to about 100:1, such as, without limitation, about 1:10, about 1:20, about 1:30, about 1:40, about 1:50, about 1:60, about 1:70, about 1:80, about 1:90, about 90:1, about 80:1, about 70:1, about 60:1, about 50:1, about 40:1, about 30:1, about 20:1, about 10:1, and any suitable ratio in between. In an embodiment, the ratio may be in a weight range of about 1:10 to about 10:1. The exact ratio of organosilane quaternary compound to quaternary ammonium compound will be determined by, for instance, the type of organosilane quaternary compound and quaternary ammonium compound used in the composition, the particular use and surface or material to which the composition is applied, as well as the specific nature of the microorganism contamination or potential microorganism contamination. The ratio of these compounds to use would be readily determinable by one skilled in the art.

The OSQAC/QAC compositions of the present invention may further comprise one or more of an oxidizing agent, a chelating agent, a surfactant, a softener, a detergent, a binder, a wetting agent, a fragrance, a scent, a dye, an antimigrant, an antifoaming agent, and/or a stabilizing agent.

The oxidizing agent may be any oxidizing agent suitable for use in a biocide or in an antimicrobial composition known to one skilled in the art. Examples of oxidizing agent include, without limitation, hydrogen peroxide, chlorine-based oxidizing agent (e.g., chlorine, chlorine dioxide, sulfur dioxide, oxygen, ozone), and a bromine-based oxidizing agent. In one embodiment, the oxidizing agent may be hydrogen peroxide. In another embodiment, the composition of the present invention may contain hydrogen peroxide in a concentration range of about 1-5%, or about 1.8-2.2%.

As used herein, the term surfactant (or surface-active agent) refers to any compound which, when dissolved in water or a water-containing solution, reduces surface tension of the solution or the interfacial tension between water or the water-containing solution and another liquid, or between water, a water-containing solution, or another liquid and a solid. Surfactants can be classified as anionic, zwitterionic or non-ionic, depending on the overall charge that the molecule carries.

Examples of nonionic surfactants include alcohol ethoxylates such as C(8) to C(18) alcohol ethoxylates containing from about 3 to 50 moles of ethylene oxide per molecule; C(8) to C(18) fatty acid esters and amides containing from about 2 to 50 moles of ethylene oxide; C(8) to C(18) fatty alcohols; C(8) to C(18) diols such as tetramethyl decynediol and dimethyl octynediol; block copolymers of polyethylene oxide and polypropylene oxide; C(8) to C(18) fatty acid esters of glycerine; ethoxylated and propoxylated C(8) to C(18) fatty alcohols; C(8) to C(18) fatty amine and amidoamine oxides; C(8) to C(18) fatty amides and alkanolamides; and alkyl saccharides (e.g., alkyl glucosides) or alkenyl-saccharides.

Examples of amphoteric surfactants include amine oxides, C(8) to C(18) sultaines such as coco-sultaine and cocamidopropyl hydroxysultaine; C(8) to C(18) fatty derivatives of amino acids such as cocamphocarboxyglycinate and lauramphoglycinate; C(8) to C(18) alkyl betaines such as decyl betaine, coco-betaine, lauryl betaine, myristyl betaine and stearyl betaine; and C(8) to C(18) amidoalkyl betaines such as cocoamidoethyl betaine, cocamidopropyl betaine, lauramidopropyl betaine, myristamidopropyl betaine and oleamidopropyl betaine. Sarcosine surfactants such as C(8) to C(18) alkyl sarcosines and their alkali metal or ammonium salts such as sodium, potassium, lithium or ammonium C (8) to C (18) alkyl sarcosinates are also contemplated by the present invention.

Examples of cationic surfactants include quaternary ammonium compounds which contain at least two nitrogen-bonded alkyl chains having at least about 16 carbon atoms such as distearyldimonium chloride and ditallowdimonium chloride; C(8) to C(18) fatty alkyl amines, amidoalkylamines and amidoalkanolamines, and their salts; ethoxylated amines; amine oxides; and immidazoline.

Examples of anionic surfactants useful in the formulations of the present invention include alkyl sulphates, alkyl or alkane sulphonates, linear alkyl benzene or naphthalene sulphonates, secondary alkane sulphonates, alkyl ether sulphates or sulphonates, alkyl phosphates or phosphonates, dialkyl sulphosuccinic acid esters, sugar esters (e.g., sorbitan esters), C(8-10) alkyl glucosides, alkyl carboxylates, paraffin sulphonates sulphosuccinate esters and sulphated linear alcohols.

Zwitterionic or amphoteric surfactants useful with the formulations include beta-N-alkylaminopropionic acids, n-alkyl-beta-iminodipropionic acids, imidazoline carboxylates, n-alky-betaines, amine oxides, sulphobetaines and sultaines.

The surfactant can optionally be present in the composition of the present invention in amounts of from about 0% to about 30% by weight, or from about 0.1% to 15% by weight or from about 2% to about 10%, or from about 1.0% to about 5.0% by weight.

Chelating agents of the present invention include inorganic and organic compounds. The chelating agent used may depend upon the specific application. Application specific concerns include cost, nature of the metal ions to be chelated, compatibility with the components of the composition, and solubility in the composition. Chelating agents of the present invention are generally non-toxic to animals and humans in the amounts described herein. One skilled in the art would be able to appreciate these parameters and select the appropriate chelating agent without undo experimentation.

In one embodiment, chelating agents of the present invention would have a complex formation equilibrium constant of about $10^7$ to about $10^{27}$. In another embodiment, the chelating agent used in the composition has a complex formation constant of about $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$, $10^{21}$, $10^{23}$, $10^{24}$, $10^{25}$, $10^{26}$, and $10^{27}$.

A safe and effective amount of one or more chelating agents may be added to the compositions of the present invention, and when present comprising about 0.1% to about 10% by weight of the composition. In another aspect, the composition comprises from about 1% to about 5% by weight of each of at least one chelating agents. In yet another aspect, the biocidal composition comprises from about 1% to about 5% by weight of a single chelating agent. In one embodiment, the biocidal composition comprises, by weight, about 0.50%, 0.75%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, and 5.0% of one chelating agent. In a further aspect, the biocidal composition comprises, by weight, about 0.50%, 0.75%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, and 5.0% of the combination of all chelating agents, wherein the composition comprises two or more chelating agents.

In one aspect, exemplary chelating agents of the present invention include carboxylic acids, polycarboxylic acids, amino acids and phosphates, such as, acetic acid; adenine; adipic acid; ADP; alanine; B-alanine; albumin; arginine; ascorbic acid; asparagine; aspartic acid; ATP; benzoic acid; n-butyric acid; casein; citraconic acid; citric acid; cysteine; dehydracetic acid; desferri-ferrichrysin; desferri-fertichrome; desferri-ferrioxamin E; 3,4-dihydroxybenzoic acid; diethylenetriaminepentaacetic acid (DTPA); dimethylglyoxime; O,O-dimethylpurpurogallin; EDTA; formic acid; fumaric acid; globulin; gluconic acid; glutamic acid; glutaric acid; glycine; glycolic acid; glycylglycine; glycylsarcosine; guanosine; histamine; histidine; 3-hydroxyflavone; inosine; ino sine triphosphate; iron-free ferrichrome; isovaleric acid; itaconic acid; kojic acid; lactic acid; leucine; lysine; maleic acid; malic acid; methionine; methylsalicylate; nitrilotriacetic acid (NTA); ornithine; orthophosphate; oxalic acid; oxystearin; B-phenylalanine; phosphoric acid; phytate; pimelic acid; pivalic acid; polyphosphate; proline; propionic acid; purine; pyrophosphate; pyruvic acid; riboflavin; salicylaldehyde; salicyclic acid; sarcosine; serine; sorbitol; succinic acid; tartaric acid; tetrametaphosphate; thiosulphate; threonine; trimetaphosphate; triphosphate; tiyptophani; uridine diphosphate; uridine triphosphate; n-valeric acid; valine; xanthosine.

In another aspect, exemplary chelating agents of the present invention include, but are not limited to, ethylenediamine tetraacetic acid (EDTA) or its salts (e.g. EDTA, sodium salt), phosphonates, nitrilotriacetic acid (NTA) or its salts, hydroxyethylene diamine and triacetic acid (HEDTA) or its salts, and diethylene triamine pentaacetic acid (DTPA) or its salts, citric acid, salicylates (e.g., sodium salicylate, 5-methoxysalicylate and homovanilate), N-amino acyl derivatives of beta-diketones (enamines), triethylene tetramine dihydrochloride (TRIEN), ethylene glycol bis(2-aminoethyl ether)-N,N,N'N'-tetraacetic acid (EGTA), triethylenetetramine hexaacetic acid (TTG), deferoxamine, dimercaprol, edetate calcium disodium, zinc citrate, penicillamine succimer and sodium editronate or any other chelating agent that will chelate divalent ions such as $Ca^{+2}$, $Mg^{+2}$, $Mn^{+2}$, $Fe^{+2}$, and $Zn^{+2}$.

In a further aspect, exemplary chelating agents of the present invention include acetoacetamide, ammonium carbamate, ammonium pyrrolidinedithiocarbamate (APDC), dimethyl malonate, methyl acetoacetate, N-methyl acetoacetamide, 2,4-pentanedione, tetramethylammonium thiobenzoate, 1,1,1,5,5,5-hexafluoro-2,4-pentanedione H(hfac), 2,2,6,6-tetramethyl-3,5-heptanedione H(thd), tetramethylammonium trifluoroacetate, tetramethylthiuram disulfide (TMTDS), trifluoracetic acid, lactic acid, ammonium lactate, malonic acid, formic acid, acetic acid, propionic acid, gamma-butyrolactone, methyldiethanolammonium trifluoroacetate, trifluoroacetic acid, and tetramethylammonium thiobenzoate.

In one embodiment, the present invention comprises a composition comprising, by weight, about 0.50%, 0.75%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, and 5.0% of EDTA.

In general, a reducing agent is a chemical which can provide an electron, or be an electron donor. Reducing agents in the present invention include, but are not limited to, hydrogen peroxide.

Antimicrobial compositions comprise solid particulate matter, including but not limited to, siliceous materials such as perlite, ceramic spheroids, hollow glass spheres, polymeric type media and thermoset coated glass spheres. Perlite is a generic name for a naturally occurring volcanic glass that when heated, expands from four to twenty times its original volume. Perlite is generally referred to as course (grain size 1.5 mm-6.0 mm), normal/medium (0.1-3.0 mm), and fine/very fine (0.0-0.2 mm). It is composed primarily of silicon($SiO_2$), 72-76%, free moisture-0.5%, aluminum ($Al_2O_3$): 11-17%, calcium (CaO): 0.5-2.0%, magnesium (MgO), iron ($Fe_2O_3$): 0.5-1.5%, potassium 4-5%, sodium: 3-4%.

In one embodiment, the present invention provides an OSQAC/QAC composition comprises about 50-80% water; organosilane quaternary compounds in a concentration range of about 0.1-10%; quaternary ammonium compounds in a concentration range of about 0.01-5%; EDTA in a concentration range of about 1-5%; hydrogen peroxide in a concentration range of about 1-5%; isopropyl alcohol (IPA) in a concentration range of about 1-10%; glycol ether DB in a concentration range of about 1-10%; and NP-9 in a concentration range of about 1-10%, and this composition is admixed with solid particulate matter, such as perlite, allowed to dry to form coated solid particulate matter, such as coated perlite. In another embodiment, the present invention provides a composition comprising solid particulate matter such as perlite and an OSQAC/QAC composition that comprises about 60-70% water; organosilane quaternary compounds in a concentration range of about 3-6%; quaternary ammonium compounds in a concentration range of about 0.1-4%; EDTA at a concentration of range of about 1.8-2.2%; hydrogen peroxide at a concentration range of about 1.8-2.2%; isopropyl alcohol at a concentration range of about 5-7%; glycol ether DB at a concentration range of about 5-7%; and NP-9 at a concentration range of about 2-4%. In another embodiment, the present invention comprises a composition comprising solid particulate matter such as perlite and an OSQAC/QAC composition comprising about 80-98% water, organosilane quaternary compound (72% Active) in concentration range of about 0.01-1%; quarternary ammonium compound in a concentration range of about 0.01-3%; isopropyl alcohol in a concentration range of about 0.01-3%; Glycol Ether DB about 0.01-5%; Barlox about 0.01-5%; hydrogen peroxide (50%) about 0.01-2%; NP-9 in concentration of about 0.01-2%: and EDTA about 0.01-2%. Glycol Ether DB is also known as Diethylene glycol monobutyl ether (DGBE) or 2-(2-Butoxyethoxy)ethanol. Barlox is a tradename for amine oxides, made by Lonza, and these are surfactants, which may find use in a variety of markets: household cleaners, personal care products and others. NP-9 is a tradename for a nonionic surfactant, made by Dow Chemical, a nonionic surfactant, nonylphenol ethoxylate.

In general, an antimicrobial or biocidal treated solid particulate matter composition is made by admixing an OSQAC/QAC composition comprising an aqueous solution of at least an organosilane compound and a quarternary ammonium compound, such as those taught herein, and a solid material, such as perlite, for an amount of time sufficient for the solid to contact the OSQAC/QAC composition. Any of the compositions taught herein can be used in the methods for treating the material. As used herein, material for treating may be discrete particulate material such as perlite or it may be any solid material having at least one surface capable of being contacted by the liquid compositions taught herein. The material may be pretreated or may not be pretreated. Dyes may be added to the compositions for visual confirmation of presence of the composition on the solid material. Initial treatments may be applied by one method, such as complete immersion of the solid in a solution, and subsequent treatments may be by spraying, or running solution through the solid material while in situ. Multiple or repeated treatments may occur wherein the OSQAC/QAC composition is applied to or provided to solid material, such as perlite, multiple times. Such applications may occur once every time interval, such as once a year, or there may be applications that serially follow each other in a short time period.

For example, expanded perlite siliceous rock (coarse type) was mixed in an aqueous solution containing a stabilized organosilane quaternary compound for a time sufficient to allow the compound to contact the perlite material, part A. Part A was prepared to form an antimicrobial effective complex comprising (0.75% TMSQ & 99.25% D. I. water solution by weight, which makes this solution ¾% active by w/v). A second composition that has both disinfectant (contact efficacy) and residual antimicrobial efficacy, and which comprises about 1% active by weight (part B), was added to part A while contacting the perlite. In general, this second solution is added at a ratio of 2 parts A to 1 part B. The perlite was mixed and agitated in the combined aqueous solution for at least several minutes to allow contact. Other methods for contacting the solid material and the solutions are contemplated by the present invention and include, but are not limited to, spraying, forced immersion, and centrifugal inundation. The treated perlite then was drained and removed to dry at room temperature. Other drying methods can also be employed.

Methods of the present invention comprise using treated particulate matter such as perlite to render substances that contact the treated particulate matter, e.g., perlite, substantially free of microbial contamination. For example, antimicrobial compositions of the present invention, comprising perlite coated or treated with OSQAC/QAC compositions may be used in removal of microbes found in solids, liquids or gases that subsequently contact the treated or coated perlite. Such treatment of solids, liquids or gases that subsequently contact the treated perlite may include antimicrobial and antibiocidal activity whereby microbial lifeforms are killed or inhibited from growing in the solids, liquids or gases after contact with the antimicrobial perlite. Methods comprise contacting a biocidal-treated surface, such as treated perlite, with a liquid or gas to render the liquid or gas free from at least a portion of the microorganisms present in the liquid or gas.

Uses of the present invention comprise uses of antimicrobial compositions of the present invention, for example, comprising perlite treated or coated with an OSQAC/QAC composition, for any physical, chemical and mechanical means of eliminating bacteria and other microorganisms from solids, liquids or gases that subsequently contact the treated surface of the particulate matter.

The present invention comprises methods of treating solids, liquids or gases that subsequently contact a surface, such as perlite, that has been treated with an OSQAC/QAC composition or by a method taught herein.

Compositions of the present invention comprise product formulations comprising the perlite treated or coated with OSQAC/QAC compositions which may be used for cleaning and/or disinfecting surfaces, including bodies or humans or animals, or clothing or bedding, or house hold cleaners, carpet cleaners, or cleansers for surfaces found in or around where humans or animals live or work, including but not limited to hand soaps and creams, shampoos and conditioners, household cleaning products, carpet cleaners, upholstery cleaners, laundry detergents, automobile or animal carrier cleansers, rinses, gels, and other formulations for cleaning or treating surfaces of humans or animals or surfaces that they touch or that touch them.

In another aspect, the present invention provides methods of disinfecting an article such as perlite and a method of providing an antimicrobial coating to perlite, including the step of contacting perlite with a composition having antimicrobial activity, where the composition comprises an organosilane quaternary compound and a quaternary ammonium compound, and where the quaternary ammonium compound is not an organosilane quaternary compound.

The compositions of the present invention may be used to disinfect a surface or a material contaminated with virus or viral particles. For example, the surface may be contaminated with the highly pathogenic H5N1 avian influenza virus, among other pathogenic agents such as *Bacillus anthraces* (anthrax) and *Bacillus atrophaeus* spores. The materials and compositions of the present invention may also be used to disinfect surfaces/materials contaminated with gram positive bacteria (e.g., *Staphylococcus aureus*), gram negative bacteria (e.g., *E. Coli* and *Pseudomonas aeruginosa*), fungi (e.g., *Aspergillus niger*), yeasts (e.g., *Candida albicans*), and algae.

A variety of surfaces and materials may be treated using the OSQAC/QAC compositions of the present invention, including, without limitation, surfaces and materials in commercial or industrial environments. Examples of such treatments include, but are not limited to, treatment of poultry houses including cages and equipment, farm and transportation vehicles for animals, foot and tire dips, walls, ceilings, floors, and fixtures found in food processing plants, refrigerators and coolers, surfaces found in broiler and breeder farms, hatchers, setters, evaporative coolers, humidifying systems, and ceiling fans found in hatcheries, surfaces found in zoos, emergency vehicles, homes, offices and automobiles, hotels, motels, schools, day care centers, hospitals, contagious illness rooms, and correctional facilities.

The compositions of the present invention may be applied to surfaces or materials such as perlite using any means suitable for the particular purpose which is known in the art, such as, without limitation, by soaking, impregnating, mixing, painting, spraying, injecting, and via aerosols. In one embodiment, the compositions of the present invention may be used to impregnate or coat surfaces or materials such as perlite. Examples of such articles include, without limitation, outwear apparel, underwear and intimate apparel, hosiery and socks, bed sheets, blankets, bedspreads, curtains and draperies, carpets, rugs, throw rugs, toweling, toilet tank covers, floor and door mats, shower curtains, athletic and casual wear, athletic and casual shoes or shoe insoles, indoor and outdoor awnings including umbrellas, upholstery, vacuum cleaner bags and filters, vinyl paper-wallpaper, mattress pads and ticking, abrasive and polishing buffer pads, fire hose fabric, fiberfill, air filters, sand bags, tents, tarpaulins, sails, and ropes, multipurpose disposal wiping cloths, pre-moistened towelettes and tissue wipes, non-woven disposable diapers, non-woven materials used for personnel, masks, hats, gloves, footwear, and protective gear or gowns. In one embodiment, the compositions of the present invention may further comprise compounds and materials readily known in the art that are useful to allow the compositions of the present invention to be applied during manufacture of materials, such as, without limitation, paper, textile, perlite and non-woven fabrics. In another embodiment, the composition of the present invention may further comprise compounds and materials readily known in the art that are useful to allow the compositions of the present invention to be applied to a finished article. For example, the compositions of the present invention may be used to treat fabrics, such as military fatigues, and are capable of preventing attachment and growth of bacteria and spores, and thus protecting the humans wearing the clothing.

As used herein, the terms antimicrobial and biocidal are overlapping and interchangeable terms, and are intended to encompass both the ability to kill and inhibit the growth of microbial lifeforms.

The term alkyl as used herein refers to a branched or unbranched saturated hydrocarbon group of 1 to 24 carbon atoms, such as methyl (Me), ethyl (Et), n-propyl, isopropyl, n-butyl, isobutyl, t-butyl, octyl, decyl, tetradecyl, hexadecyl, eicosyl, tetracosyl and the like. Exemplary alkyl groups herein contain from 1 to 12 carbon atoms. The term lower alkyl intends an alkyl group of from one to six carbon atoms, preferably from one to four carbon atoms. The term cycloalkyl intends a cyclic alkyl group of from three to eight, preferably five or six carbon atoms. Lower alkyl alcohol refers to lower alkyl having attached thereto one or more hydroxy moieties, such as, but not limited to, —$CH_2CH_2OH$, $CH_2CH(OH)CH_3$, $CH_2OH$, $CH_2CH_2CH_2OH$, $CH_2CH_2CH(OH)CH_3$, $CH_2CH_2CH(OH)CH_2OH$, or $CH_2CH(OH)CH(OH)CH_3$.

The term alkoxy as used herein intends an alkyl group bound through a single, terminal ether linkage; that is, an alkoxy group may be defined as OR where R is alkyl as defined above. A lower alkoxy group intends an alkoxy group containing from one to six, more preferably from one to four, carbon atoms. Polyether refers to a compound or moiety possessing multiple ether linkages, such as, but not limited to, polyethylene glycols or polypropylene glycols. Polyalkylethers refers to alkyls interconnected by or otherwise possessing multiple ether linkages.

As used herein, optional or optionally means that the subsequently described event or circumstance may or may not occur, and that the description includes instances where said event or circumstance occurs and instances where it does not. For example, the phrase optionally substituted lower alkyl means that the lower alkyl group may or may not be substituted and that the description includes both unsubstituted lower alkyl and lower alkyl where there is substitution.

By the term effective amount of a compound, product, or composition as provided herein is meant a sufficient amount of the compound, product or composition to provide the desired result. As will be pointed out below, the exact amount required will vary from substrate to substrate, depending on the particular compound, product or composition used, its mode of administration, and the like. Thus, it is not always possible to specify an exact effective amount. However, an appropriate effective amount may be determined by one of ordinary skill in the art using only routine experimentation.

The term aryl as used herein refers to a compound or moiety whose molecules have a ring or multiple ring structure characteristic of benzene, naphthalene, phenanthrene, anthracene, etc., i.e., either the six-carbon ring of benzene or the condensed six-carbon rings of the other aromatic derivatives, including, but not limited to phenyl, benzyl, naphthyl, benzylidine, xylil, styrene, styryl, phenethyl, phenylene, benzenetriyl, etc. As used herein, the term aromatic refers to the group of unsaturated cyclic hydrocarbons, typified by benzene, having a 6-carbon ring containing three double bonds or multiple attached benzene rings. Moreover, certain five membered cyclic compounds, such as furan (heterocyclic), are analogous to aromatic compounds. Aromatics include the cyclic compounds based upon a benzene functionality, as specified for aryl above. Moreover, the term cyclic is used to refer to all aliphatic or aromatic hydrocarbons having one or more closed rings, whether unsaturated or saturated. Preferably, cyclic compounds possess rings of from 5 to 7 carbon atoms, preferably 6 carbon atoms. Such rings fall into three classes: alicyclic, aromatic (arene), and heterocyclic. Moreover, when used with respect to cyclic compounds or moieties, the term unsaturated refers to such compound or moiety possessing at least one double or triple bond or otherwise constituting an aromatic compound or moiety. Moreover, the term saturated refers to compounds or moieties possessing no double or triple bonds, i.e., where all available valence bonds of an atom, especially carbon, are attached to other atoms.

The term heteroaryl refers to an aryl where one or more of the carbon atoms of a ring have been substituted with a heteroatom, including, but not limited to, O, N, or S. Similarly, the term heterocyclic refers to a cyclic compound or moiety where one or more of the carbon atoms of the ring has been substituted with a heteroatom, including, but not limited to, O, N, or S.

As used herein, especially in reference to alkyl and alkoxy, the term lower refers to a moiety having from 1 to 6 carbon atoms, preferably 1 to 4 carbon atoms.

As used herein, the term suitable is used to refer a moiety which is compatible with the compounds, products, or compositions as provided herein for the stated purpose. Suitability for the stated purpose may be determined by one of ordinary skill in the art using only routine experimentation.

As used herein, substituted is used to refer, generally, to a carbon or suitable heteroatom having a hydrogen or other atom removed and replaced with a further moiety. In one embodiment, halogen, hydroxy, and nitrogen based substitutions of hydrocarbon hydrogens are contemplated as within the scope of the present invention for the claimed structures. Moreover, it is intended that substituted refer to substitutions which do not change the basic and novel utility of the underlying compounds, products or compositions of the present invention. Unsubstituted refers to a structure wherein the reference atom does not have any further moieties attached thereto or substituted therefor.

As used herein, branched is used to refer, generally, to a moiety having a carbon chain backbone, e.g., alkyl or alkoxy, wherein the backbone may contain one or more subordinate carbon chain branches. For example, isobutyl, t-butyl, isopropyl, $CH_2CH_2C(CH_3)(H)CH_2CH_3$, $CH_2C(CH_2CH_3)(H)CH_2CH_3$, $CH_2CH_2C(CH_3)_2CH_3$, and $CH_2CH_2C(CH_3)_3$ would all be considered branched moieties. Moreover, it is intended that branched variations of the moieties herein described refer to variations which do not change the basic and novel utility of the underlying compounds, products or compositions of the present invention. Unbranched refers to a structure wherein the carbon chain does not have any branches thereon, i.e., where the carbon chain extends in a direct line.

As used herein, the term acyl refers to organic acid derived moieties of the formula RCOX where R is an organic molecule and X, instead of being hydroxy, is replaced with another substituent, preferably, a suitable anion, such as a halogen including, but not limited to, F, Cl, Br or I.

As used herein, the term perfluoro or perfluoro-analog refers to a hydrocarbon where the hydrogen atoms attached to carbons have been replaced with F atoms. Preferably, but not necessarily, in perfluoro-analogs, most if not all of the H atoms are replaced with F atoms. A fluoro analog is contemplated to indicate a hydrocarbon where at least one hydrogen atom attached to a carbon is replaced with an F atom.

As used herein, substrate refers to any article, product, or other surface that can be treated with the inventive compounds. Suitable substrates are generally characterized in preferably having a negatively charged surface of oxygen atoms, or any surface capable of electrostatically, ionically or covalently adhering or binding to the compounds, products, or compositions of the present invention. The adhering or binding may occur at the silicon atom of the organosilane portion of the compounds, products, or compositions of the present invention, but such binding is not a requirement. Therefore, as used herein, the term adhere is meant to refer to ionic, covalent, electrostatic, or other chemical attachment of a compound, product or composition to a substrate.

As used herein, the term biocidal is used in its general sense to refer to the property of the described compound, product, composition or article to kill, prevent or reduce the growth, spread, formation or other livelihood of organisms such as bacteria, viruses, protozoa, fungi, molds, algae, or other organisms likely to cause spoilage, disease or infection.

As used herein, the term chelating agent refers to any organic or inorganic compound that will bind to or form a complex with a metal ion having a valence greater than one. The term metal ions, as used herein, includes alkali, alkaline earth, and transition metal ions. Examples of metal ions of interest in connection with the present invention include, but are not limited to, $Ca^{+2}$, $Mg^{+2}$, $Mn^{+2}$, $Fe^{+2}$, and $Zn^{+2}$.

As used herein, the term stabilizer is used to refer to the class of polyols as specified herein wherein any two of the at least three hydroxy groups are separated by at least three atoms. Such compounds have been found to stabilize the organosilanes by preventing self-condensation or other inactivation of the resulting compounds and products.

Finally, there terms halogen are used to refer to Fluorine F, Chlorine Cl; Bromine Br, Iodine I, and Astatine At Preferably, halogen or halide refers to F, Cl, or Br. The term halide is meant to include these halogens.

As used herein and in the appended claims, the singular forms "a," "an," and "the" include plural references, unless the content clearly dictates otherwise. Thus, for example, reference to "a stabilizer agent" includes a plurality of such stabilizer agents and equivalents thereof known to those skilled in the art, and reference to "the chelating agent" is a reference to one or more chelating agents and equivalents thereof known to those skilled in the art, and so forth. All publications, patent applications, patents, and other references mentioned herein are incorporated by reference in their entirety.

It is to be understood that the terminology used herein is for the purpose of describing particular embodiments only and is not intended to be limiting. It must be noted that, as used in the specification and the appended claims, the singular forms a, an and the include plural referents unless the context clearly dictates otherwise.

Throughout this application, where publications are referenced, the disclosures of these publications in their entireties are hereby incorporated by reference into this application in order to more fully describe the state of the art to which this invention pertains.

The following Examples are provided as illustrative of the uses and applications of the present invention to add one skilled in the art. The Examples are not to be considered limiting or restricting to the uses of the present invention.

EXAMPLES

Example 1

Preparation of Perlite Antimicrobial Treated Surfaces with Antimicrobial Properties 350 grams of expanded coarse perlite (8.0-12.0 pounds per cubic foot) was mixed with stirring solution comprising 0.75% (w/v) water-stabilized 3-(trimethoxysilyl)propyl-dimethyloctadecyl ammonium chloride (TMSAC). The pH of the treatment solution was about 6.5. The amount of perlite used was about 1 liter, and the amount of TMSAC used was about 1 gallon. Initially, the perlite was manually submerged. The temperature of the solution was about 70-75° C.

After stirring the perlite and TMSAC solution for 15-30 minutes, an equal volume of a second solution was added and stirring was allowed to continue for an additional 15-30 minutes. The second solution was:

| Component | Percent (w/w) |
|---|---|
| 3-(trihydroxysilyl) propyldimethyl octadecyl ammonium chloride | 0.50 |
| N,N Diakyl(C8–C10)-N,N-dimethylammonium chloride | 0.75 |
| N-Alkyl(50% C14, 40% C12, 10% C16) dimethylbenzylammonium chloride | 0.75 |
| Isopropyl alcohol | 0.75 |
| Glycol Ether EB | 0.75 |
| Barlox | 0.67 |
| EDTA | 0.25 |
| T-NP-9.5 Surfactant | 0.38 |
| Water | 95.20 |

The perlite was then removed from the solution and was dried at room temperature.

Example 2

The treated perlite from Example 1 is used to remove bacterial contamination from a liquid. An amount of treated perlite that is effective for contacting the water is added to a standing body of contaminated water for a sufficient time. A first bacterial count, made before the addition of the treated perlite, is compared to a second bacterial count made after contact with the treated perlite. A lower number of bacteria are found in the second bacterial count.

Whereas this invention has been described in detail with particular reference to specific embodiments, it will be apparent to those skilled in the art that various modifications and variations can be made in the present invention in light of the above teachings without departing from the scope or spirit of the invention. Other embodiments of the invention will be apparent to those skilled in the art from consideration of the specification and practice of the invention disclosed herein. It is intended that the specification and examples be considered exemplary only, with a true scope and spirit of the invention being indicated by the following claims.

What is claimed is:

1. An antimicrobial composition, comprising:
perlite coated with a composition comprising approximately 4% by weight an organosilane quaternary ammonium compound and approximately 2% by weight a quaternary ammonium compound,
wherein the quaternary ammonium compound is not an organosilane quaternary ammonium compound;
wherein the organosilane quaternary ammonium compound is 3-trimethoxysilyl propyltetradecyldimethyl ammonium chloride; and
wherein the quaternary ammonium compound is a mixture of alkyl (C12, C14 and C16) dimethyl benzyl ammonium chloride, octyl decyl dimethyl ammonium chloride, dioctyl dimethyl ammonium chloride and didecyl dimethyl ammonium chloride.

2. The antimicrobial composition of claim 1, wherein the composition further comprises at least one agent selected from the group consisting of an oxidizing agent, a chelating agent, and a stabilizing agent.

3. The antimicrobial composition of claim 2, wherein the oxidizing agent is hydrogen peroxide.

4. The antimicrobial composition of claim 2, wherein the chelating agent is ethylenediaminetetraacetic acid (EDTA) or a salt thereof 5. The antimicrobial composition of claim 2, wherein the stabilizing agent is propylene carbonate, glycol ether, a polyol, or sucrose.

6. A method of rendering perlite antimicrobial comprising:
contacting perlite with an aqueous composition, wherein the aqueous composition comprises approximately 4% by weight of an organosilane quaternary ammonium compound and approximately 2% by weight of a quaternary ammonium compound, and wherein the quaternary ammonium compound is not an organosilane quaternary ammonium compound; and
bonding at least a portion of the aqueous composition to at least a portion of the perlite to form an antimicrobial coating on the perlit,
wherein the organosilane quaternary ammonium compound is 3-trimethoxysilyl propyltetradecyldimethyl ammonium chloride; and
wherein the quaternary ammonium compound is a mixture of alkyl (C12, C14 and C16) dimethyl benzyl ammonium chloride, octyl decyl dimethyl ammonium chloride, dioctyl dimethyl ammonium chloride and didecyl dimethyl ammonium chloride.

7. The method of claim 6, wherein the aqueous composition further comprises at least one agent selected from the group consisting of an oxidizing agent, a chelating agent, or a stabilizing agent.

8. The method of claim 7, wherein the oxidizing agent is hydrogen peroxide.

9. The method of claim 7, wherein the chelating agent is ethylenediaminetetraacetic acid (EDTA) or a salt thereof.

10. The method of claim 7, wherein the stabilizing agent is propylene carbonate, glycol ether, a polyol, or sucrose.

11. A method of removing a portion of microbes present in a gas, liquid or solid, comprising:
contacting the gas, liquid or solid with a composition having antimicrobial activity, the composition having antimicrobial activity comprising perlite coated by an aqueous composition comprising approximately 4% by weight of an organosilane quaternary ammonium compound and approximately 2% by weight of a quaternary ammonium compound,
wherein the quaternary ammonium compound is not an organosilane quaternary ammonium compound;
wherein the organosilane quaternary ammonium compound is 3-trimethoxysilyl propyltetradecyldimethyl ammonium chloride; and
wherein the quaternary ammonium compound is a mixture of alkyl (C12, C14 and C16) dimethyl benzyl ammonium chloride, octyl decyl dimethyl ammonium chloride, dioctyl dimethyl ammonium chloride and didecyl dimethyl ammonium chloride.

12. The method of claim 11, wherein the aqueous composition further comprises at least one agent selected from the group consisting of an oxidizing agent, a chelating agent or a stabilizing agent.

* * * * *